United States Patent
Su

Patent Number: 5,693,604
Date of Patent: *Dec. 2, 1997

[54] AQUEOUS BODY CLEANSING COMPOSITION CONTAINING AMPHOCARBOXYGLYCINATE, ETHOXY SULFATE, SOAP, ACYLATED PROTEIN SALT AND ACYL GLUTAMATE

[75] Inventor: Dean T. Su, Princeton Junction, N.J.

[73] Assignee: Colgate-Palmolive Company, New York, N.Y.

[*] Notice: The term of this patent shall not extend beyond the expiration date of Pat. No. 5,387,372.

[21] Appl. No.: 373,166

[22] Filed: Jan. 17, 1995

Related U.S. Application Data

[63] Continuation of Ser. No. 26,924, Mar. 5, 1993, Pat. No. 5,387,372.

[51] Int. Cl.$^6$ .................. C11D 1/94; C11D 1/32; C11D 9/36
[52] U.S. Cl. .............. 510/499; 510/130; 510/137; 510/138; 510/159; 510/490; 510/477; 510/480; 510/495; 510/506; 510/483; 510/475
[58] Field of Search ............... 252/546, 547, 252/548, 174.23, 174.15, 117, DIG. 13, DIG. 5, 130, 137, 138, 159, 490, 477, 480, 495, 506, 483, 475

[56] References Cited

U.S. PATENT DOCUMENTS

| | | | |
|---|---|---|---|
| 4,477,375 | 10/1984 | Grollier | 252/542 |
| 4,540,507 | 9/1985 | Grollier | 252/174.23 |
| 4,664,835 | 5/1987 | Grollier et al. | 252/90 |

Primary Examiner—Paul Lieberman
Assistant Examiner—Charles I. Boyer
Attorney, Agent, or Firm—Martin B. Barancik

[57] ABSTRACT

1. In accordance with the invention there is an aqueous composition comprising a. about 5–10 wt % of

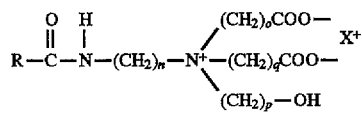

wherein R is alkyl and/or alkenyl having an average of from about 8 to 18 carbon atoms, inclusive;

n is 1, 2 or 3;

o, p and q are the same or different and are 1, 2 or 3;

X is an alkali metal or amine cation;

b. about 1 to 8 wt % of $R^1-(OCH_2CH_2)_m-OSO_3^-Y^+$ wherein $R^1$ is alkyl and/or alkenyl of about 8 to 18 carbon atoms, inclusive;

m is 0 or 1–10, y is an alkali metal or amine cation;

c. about 0.5 to 5 wt % of a soap;

d. about 1 to 5 wt % of an acylated hydrolyzed protein salt wherein the acyl group is alkyl and/or alkenyl carboxy acyl having an average number of carbon atoms of about 8 to 20 carbon atoms, inclusive; and e. about 0.1–5 wt % of an acyl glutamate salt wherein the acyl group is alkyl and/or alkenyl carboxy acyl having an average number of carbon atoms of from about 8 to 20 carbon atoms, inclusive.

9 Claims, No Drawings

AQUEOUS BODY CLEANSING COMPOSITION CONTAINING AMPHOCARBOXYGLYCINATE, ETHOXY SULFATE, SOAP, ACYLATED PROTEIN SALT AND ACYL GLUTAMATE

This is a Continuation of application Ser. No. 08/026,924 filed Mar. 5, 1993 now issued as U.S. Pat. No. 5,387,372.

BACKGROUND OF THE INVENTION

Over the years there has been a constant evolution of cleansing compositions for the human skin. From the basic use of lye soap to the more advanced combars and synthetic detergents in both liquid and solid form, there has been a constant quest for improved compositions having better cleansing activity but with increased mildness to the skin as well as, inter alia, better sensory attributes. It has now been discovered that a new composition can be formulated which is a clear, mild, high foaming body cleanser particularly useful for the face and hands. The composition provides a proper balance of cleansing activity, foaming and mildness.

SUMMARY OF THE INVENTION

In accordance with the invention there is an aqueous composition comprising a. about 5–10 wt % of $$R-\underset{\underset{O}{\|}}{C}-\underset{\underset{H}{|}}{N}-(CH_2)_n-N^+\diagup\begin{array}{l}(CH_2)_oCOO^-\\(CH_2)_qCOO^-\\(CH_2)_p-OH\end{array}\quad X^+$$

wherein R is alkyl and/or alkenyl having an average of from about 8 to 18 carbon atoms, inclusive;

n is 1, 2 or 3;

o, p and q are the same or different and are 1, 2 or 3;

X is an alkali metal or amine cation;

b. about 1 to 8 wt % of $R^1-(OCH_2CH_2)_m-OSO_3^-Y^+$ wherein $R^1$ is alkyl and/or alkenyl having an average of about 8 to 18 carbon atoms, inclusive;

m is 0 or 1–10, y is an alkali metal or amine cation;

c. about 0.5 to 5 wt % of soap;

d. about 1 to 5 wt % of an acylated hydrolyzed protein salt wherein the acyl group is alkyl and/or alkenyl carboxy acyl having an average number of carbon atoms of about 8 to 18 carbon atoms, inclusive; and e. about 0.1–5 wt % of an acyl glutamate salt wherein the acyl group is alkyl and/or alkenyl carboxy acyl having an average number of carbon atoms of from about 8 to 18 carbon atoms, inclusive.

DETAILED DESCRIPTION OF THE INVENTION

The composition provides excellent cleansing to the body while maintaining high foaming action and low irritability.

The surfactant of formula a helps provide the formulation with appropriate cleansing activity and foaming while maintaining low irritability. Interestingly, the formulation may not become milder by adding greater than 10 wt % of this component. This group of compounds is generically known as the amphodicetates or the amphocarboxyglycinates. The R group is preferably an average of from 10 to 16 carbon atoms, inclusive and is more preferably alkyl, normal alkyl. The most preferable acyl group is the coconut acid radical. The n group is preferably 2 and o, p and q are preferably 1 or 2. Cocoamphodiacetate is commercially available from numerous companies such as Velvetex CDC from Henkel and as a portion of Miracare 2 MCT modified from Rhone-Poulenc.

The cation in this formula and also in the other anionic surfactants employed in the formulation makes the salt more water soluble. Examples of such cations include alkali metals such as sodium and potassium; and various amines such as ammonium and ammonium derivatives for example dimethyl monoethanolamine, methyldiethanolamine, trimethylamine, triethylamine, dibutylamine, butyldimethylamine, monoethanolamine, diethanolamine, triethanolamine, isopropyldimethylamine and isopropylethanolamine as well as tris (hydoxymethyl) amino methane. Preferred amines are monoethanolamine, diethanolamine and triethanolamine. A particularly preferred amine is triethanolamine.

Component b is a good counterpart to component a of the composition. Although not as mild, it is a very good foamer and surfactant. Preferably m is an integer of 1 to 4. The R group is preferably an average of about 10 to 16 carbon atoms, inclusive and is generally alkyl or normal alkyl. The preferred material is sodium trideceth sulfate and is commercially available from such sources as Rhone-Poulenc. Y is a cation of the scope as described for component a. A preferred quantity of b is about 2 to 6 wt %.

Component c is a traditional soap, that is, an alkali metal or amine salt of an alkyl and/or alkenyl long chain carboxylic acid. The fatty acid portion has an average of from about 8 to about 18 carbon atoms inclusive, preferably about 10 to 16. More than about 5 wt % of soap in the composition can bring about haziness. Clarity is achieved using less than about 5 wt % of the soap in the composition. This level also maintains the low irritancy level of the composition as well as helping to provide the excellent cleansing and foaming activity. Additionally the presence of the soap brings about a reduced residual feel following rinsing of the composition from the body. A preferred quantity of soap is from about 1 to 4 wt % of the composition.

Component d is a long chain acylated hydrolyzed protein for example an animal protein such as collagen. It is usually sold as the alkali metal salt such as sodium or potassium commercially, for example LameponS from Henkel, Foam-Coil 4C from Brooks, May—Tein C from Maybrook and the like. The long chain carboxy acyl group generally has an average of from about 8 to 20 carbon atoms in alkyl and/or alkylene groups, preferably about 10 to 18 carbon atoms in, more preferably, an alkyl group. The product is prepared by condensing an acid chloride for example coconut acid chloride with hydrolyzed collagen and then preparing the alkali metal salt or amine salt, for example potassium, thereof. The presence of the salt of the acylated hydrolyzed protein increases the mildness of the overall composition and provides good foaming properties. A preferred wt % is from about 2–4 wt % of the composition.

Finally, component e is a salt of an acylated glutamate. The acyl group is an alkyl and/or alkenyl carboxyl acyl group having an average of from about 8 to 20 carbon atoms, preferably about 10 to 18 carbon atoms. Alkyl, more preferably normal alkyl is generally employed. The salt is formed from an alkali metal or amine cation, preferably triethanolamine. The material is readily available commercially from Ajinomoto. It is generally made by condensing an acid chloride such as coconut acid chloride with glutamic acid and then preparing the salt thereof. The salt of the acylglutamate is a very mild, good foaming, good flash foaming surfactant. However it is also very "thin" viscosity wise; therefore, relatively low quantities of such a reagent are employed. Preferred quantities of about 0.2 to 3.0 wt % of the composition can be employed.

The composition utilizing these five components in the disclosed quantities brings about a formulation having an overall good balance in cleansing activity, foaming, and mildness to the skin as well as being a clear, one phase composition.

The composition according to the invention can also have optionally any one or more known agents satisfying various functions known to be useful in topical skin care, particularly for facial cleansers. Examples of these functions are additional surfactants such as anionic surfactants, nonionic, amphoteric and zwitterionic surfactants. Additional functions include agents operating as thickening agents, preservatives, emoltients, solvents, humectants, and powders. Example of these further agents appear at the aforementioned U.S. Pat. No. 5,139,781 column 5, line 35 to column 11, line 33 all of which is herein incorporated by reference into this present specification. All of the above materials can be employed as long as the clarity of the composition is preferably maintained.

Although the viscosity of the composition is not necessarily a paramount property, a viscosity which is pleasing to the feel but still allows a proper quantity of formulation to be delivered readily through an appropriately sized aperture of a hand pumped delivery apparatus is desirable. Therefore, generally a viscosity of about 1,000 to 10,000 cps, preferably about 3,000 to 7,000 cps is appropriate.

In order to obtain this desired viscosity an appropriate thickening agent can be employed. Such thickening agents are materials which will provide the desired viscosity but leave the other properties of the formulated composition essentially unchanged or perhaps even improved. Examples of such thickness modifiers are the cellulosic polymers and the acrylic polymers and copolymers. These materials preferably maintain the clearness and single phase of the composition. A specific thickening agent is Aculyn a copolymer of acrylic acid and polyethylene glycol steareth (PEG20) methacrylate available from Rohm & Haas. The quantity of thickening agent is not critical and is directly related to the desired viscosity of the composition. If present, generally no more than 5 wt %, preferably 1–3 wt % of thickener is employed.

An alcohol such as a mono ol or a glycol can also be present in the composition. Many standard multiple component compositions commercially available utilize a glycol therein for solubility purposes. For example, Miracare 2 MCT modified, a surfactant containing composition from Rhone-Poulenc, also utilizes at least one glycol therein, hexylene glycol, for purposes of solubilization. Glycols, in general, are known as humectants in the body care art. Therefore from 1 to 10 wt %, preferably 2 to 7 wt % of an alcohol, particularly a glycol, or mixtures thereof, can also be present in the composition. Example of other glycols include propylene glycol, butylene glycol, pentylene glycol and the like.

A still further component of the composition can be a silicone containing polymer which maintains the clarity and single phase of the composition. Ordinary silicones will not accomplish this. Rather it is a silicone such as dimethyl polysiloxane which has a sufficient number of ethoxyl groups thereon to bring about water solubilization so as to obtain a single clear phase. Such a siloxane need not have only ethoxyl groups but may also have other groups such as propoxyl groups up to a level wherein the clarity and single phased nature of the composition is maintained. These materials, generally known as dimethicone copolyols are classified by a manufacturer as surfactants, see Dow Corning product information, and are soluble in water, for example, Dow Corning 193. Such materials bring about properties a surfactant normally provides. It also has a silicone base. Quantities of dimethicone copolyol can be employed of from about 0.1 to 2 wt % of the composition, preferably about 0.3 to 1.5 wt % of the composition provided that the clarity and single phased nature of the composition is maintained.

Below are specific examples of the claimed invention. These examples are intended to exemplify rather than limit the invention.

EXAMPLE 1

The following composition was made by standard formulation techniques and conditions as set forth below:

Weigh Part 1 ingredients (acylated, hydrolyzed protein, amphodiacetate, trideceth sulfate, acylglutamate, soap, base, dimethicone copolyol and u.v stabilizer into a suitable container. Heat to 65°–70° C. while mixing at moderate speed. Insure that u.v. stabilizer is well-dispersed. Disperse formula amount of Aculyn Polymer 22 into formula amount of deionized water in a suitable main vessel, and mix at moderate speed. Add step 1 ingredients slowly to step 2 materials in the main vessel while mixing at moderate speed. Mix until all become homogeneous. (5–10 minute mixing is sufficient for a 1–3 kilo batch if adequately mixed.) While mixing at moderate speed, add formula amounts of tetrasodium EDTA, DMDM hydantoin, fragrance, and color at 5-minute intervals, and mix until homogeneous. Filter the finished product through 75–100 micron strainer.

The following formulation was prepared as described above.

| Component | Wt % |
|---|---|
| Acylated hydrolyzed animal protein (collagen) (30 wt %)[a] | 10.0 |
| Lauric Acid | 1.5 |
| Cocoamphodiacetate (50 wt %)[b] | 10.0 |
| Acylglutamate (30 wt %)[c] | 1.0 |
| Cocoamphodiacetate[d] | 3.75 |
| Sodium trideceth sulfate[d] | 4.5 |
| Hexylene glycol[d] | 2.25 |
| Isopropanol[d] | 0.5 |
| Triethanolamine | 1.85 |
| Benzophenone 6 | 0.03 |
| Dimethicone copolyol[e] | 0.5 |
| Deionized water | up to 100% |
| Aculyn polymer 22 (30 wt %)[f] | 7.0 |
| Fragrance | 0.3 |
| DMDM hydantoin | 0.3 |
| Tetrasodium EDTA | 0.3 |
| colorant (0.01%) | 3.0 |

[a]LameponS, as potassium salt, from Henkel
[b]Velvetex CDC from Henkel
[c]CT-12, as triethanolamine salt from Ajinomoto
[d]Used as Miracare 2MCT modified from Rhone-Poulenc which is employed at 25 wt % level in the composition. The product information sheet states that the Miracare composition is about 50% water, about 43% cocoamphodiacetate and trideceth sulfate, about 9 wt % hexylene glycol and about 2 wt % isopropanol. Sodium chloride is also present at about a six percent level. The wt % of these components in the formulation as stated above are calculated on this basis.
[e]Dimethicone copolyol is a polymeric water soluble surfactant which is an ethoxylated dimethylsiloxane obtained as Dow Corning 193 from Dow Corning.
[f]Aculyn is an acrylic acid polyethylene glycol steareth (PEG 20) methacrylate copolymer obtained from Rohm and Haas.

This formulation had a viscosity of 6480 cps. It obtained a flash foam of 575 ml, a maximum foam of 600$^+$ ml and a drainage time of 5'40". The test systems used to obtain these data are the following:

Foam height testing was performed on the above compositions as follows. 15 grams of cleanser were added to 84 grams of 250 ppm hard water and 1 gram of synthetic sebum. The hard water was prepared by mixing together 40 grams of MgCl 2.6H2O with 45 grams of CaCl 2.2H2O and diluting to 250 ppm. The synthetic sebum was prepared by melting together the following ingredients.

|  | % by Wgt. |
| --- | --- |
| Palmitic Acid | 10.0 |
| Stearic Acid | 5.0 |
| Coconut Oil | 15.0 |
| Paraffin | 10.0 |
| Spermaceti | 15.0 |
| Olive Oil | 20.0 |
| Squalene | 5.00 |
| Cholesterol | 5.00 |
| Oleic Acid | 10.0 |
| Linoleic Acid | 5.0 |
|  | 100.0 |

The test mixture was then heated with moderate agitation and slow heating to 105° F. This dispersion was then carefully poured into a 600 ml. graduated cylinder containing a plastic water-filled tube. The cylinder was then mounted onto the center of a Vertical Rotator Assembly and rotated at a constant speed of 30 rpm utilizing the action of the circular mixing of the cylinder and the free falling action of the water-filled tube in the cylinder. After 8 complete revolutions, the Flash Foam Height was measured and the Drainage Time was also measured. Drainage Time is defined as the time measured from the completion of the 20 revolutions to the time at which 100 mls. of apparent liquid has drained. Drainage Time is a measure of the wetness and stability of the foam.

The following example of the invention and comparative example were prepared in the same manner as example 1 and tested for flash foam, maximum foam and drainage time in the same manner as Example 1. All components used in the example and comparative example were from the same sources as in example 1. Below are the formulation and the results.

EXAMPLE 2

| Component | Wt % |
| --- | --- |
| Acylated hydrolyzed animal protein (30 wt %) | 10.0 |
| Lauric acid | 1.5 |
| Cocoamphodiacetate (50 wt %) | 10.0 |
| Acylglutamate (30 wt %) | 0.50 |
| Cocoamphodiacetate | 3.75 |
| Sodium trideceth sulfate | 4.5 |
| Hexylene glycol | 2.25 |
| Isopropanol | 0.5 |
| Triethanolamine | 1.85 |
| Tinuvin 328 |  |
| Dimethicone copolyol | 0.5 |
| Deionized water | up to 100% |
| Aculyn (30 wt %) | 6.75 |
| Fragrance | 0.3 |
| DMDM hydantoin | 0.3 |
| Tetrasodium EDTA | 0.2 |
| Colorant (0.01 wt %) | 3.0 |

This formulation had a viscosity of 6340 cps. It obtained a flash foam of 550 ml, a maximum foam of 600⁺ ml and a drainage time of 6'10".

COMPARATIVE EXAMPLE

The formulation of example 2 was prepared except that both acylglutamate and dimethicone copolyol were omitted and 0.5 wt % of PEG-40 hydrogenated castor oil added as a solubilization promoter.

This formulation had a viscosity of 7160 cps. It obtained a flash foam of 525 ml, a maximum foam of 595 ml and a drainage time of 3'45".

The composition of the invention is clearly superior in the measured properties.

The composition of the invention is a body care product, particularly used for cleansing hands and face, which provides an excellent balance of good cleansing activity, foaming and mildness.

I claim:

1. A clear aqueous composition consisting essentially of (a) about 5-10 wt. % of

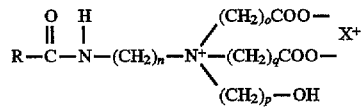

wherein R is alkyl and/or alkenyl having an average of from about 8 to 18 carbon atoms, inclusive;

n is 1, 2 or 3;

o, p and q are the same or different and are 1, 2 or 3;

X is an alkali metal or amine cation;

(b) about 1 to 8 wt. % of

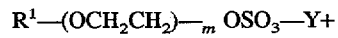

wherein $R^1$ is alkyl and/or alkenyl of about 8 to 18 carbon atoms, inclusive;

m is 0 or 1–10;

Y is an alkali metal or amine cation;

(c) about 0.5 to 5 wt. % of a soap;

(d) about 1 to 5 wt. % of an acylated hydrolyzed protein salt wherein the acyl group is alkyl or alkenyl carboxy acyl having an average number of carbon atoms of about 8 to 20 carbon atoms, inclusive; and (e) about 0.1–5 wt. % of an acyl glutamate salt wherein the acyl group is alkyl and/or alkenyl carboxy acyl having an average number of carbon atoms of from about 8 to 20 carbon atoms, inclusive.

2. The composition in accordance with claim 1 wherein a thickening agent is also present and the viscosity of the composition is about 1,000 to 10,000 cps.

3. The composition in accordance with claim 1 wherein a glycol is also present.

4. The composition in accordance with claim 1 wherein about 2 to 6 wt % of component b is present.

5. The composition in accordance with claim 1 wherein about 1 to 4 wt % of component c is present.

6. The composition in accordance with claim 1 wherein about 2 to 4 wt % of component d is present.

7. The composition in accordance with claim 1 wherein about 0.2 to 3 wt % of component e is present.

8. The composition in accordance with claim 4 wherein about 2 to 4 wt % of component c is present, about 1 to 3 wt % of component d is present, and about 0.2 to 3 wt % of component e is present.

9. The composition in accordance with claim 8 wherein about 1 to 10 wt % of a glycol is present.

* * * * *